US00PP31344P2

(12) United States Plant Patent
Smit

(10) Patent No.: US PP31,344 P2
(45) Date of Patent: Jan. 7, 2020

(54) ***SENECIO* PLANT NAMED 'EC-SENEC-1810'**

(50) Latin Name: *Senecio mikanioides*
Varietal Denomination: EC-SENEC-1810

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/350,769

(22) Filed: Jan. 4, 2019

(51) Int. Cl.
*A01H 5/02* (2018.01)
*A01H 6/14* (2018.01)

(52) U.S. Cl.
USPC ..... Plt./480
CPC ..... *A01H 6/14* (2018.05)

(58) Field of Classification Search
USPC ..... Plt./480
CPC ..... A01H 5/02; A01H 5/12
See application file for complete search history.

*Primary Examiner* — Kent L Bell

(57) ABSTRACT

A new cultivar of *Senecio* plant named 'EC-SENEC-1810' that is characterized by heart shaped leaves that have a bi-colored pattern of silver-grey and green on the upper surface and are purple in color on the lower surface.

1 Drawing Sheet

Botanical classification: *Senecio mikanioides.*
Variety denomination: 'EC-SENEC-1810'.

BACKGROUND OF THE INVENTION

The present invention relates to a new and distinct cultivar of *Senecio* plant botanically known as *Senecio mikanioides* and hereinafter referred to by the cultivar name 'EC-SENEC-1810'.

'EC-SENEC-1810' originated from the crossing of the female or seed parent, an unnamed *Senecio mikanioides* cultivar and the male or pollen parent, an unnamed *Senecio mikanioides* cultivar. The crossing was conducted in 2014 in Sappemeer, Netherlands. The resulting seeds were subsequently planted and grown. The cultivar 'EC-SENEC-1810' was selected by the inventor in 2015 in a controlled environment as a single plant within the progeny of the stated cross in a cultivated area of Sappemeer, Netherlands.

Asexual reproduction of the new cultivar 'EC-SENEC-1810' first occurred by stem cuttings in 2015 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Senecio cultivar 'EC-SENEC-1810'. These traits in combination distinguish 'EC-SENEC-1810' as a new and distinct cultivar apart from other existing varieties of *Senecio* known by the inventor.

1. *Senecio* 'EC-SENEC-1810' exhibits leaves having a bi-colored pattern of silver-grey and green on the upper surface.
2. *Senecio* 'EC-SENEC-1810' exhibits leaves having a purple color on the lower surface.
3. *Senecio* 'EC-SENEC-1810' exhibits heart shaped leaves.

The closest comparison cultivars are plants of the species *Senecio mikanioides* (not patented) and plants of the species *Senecio macroglossus* (not patented). 'EC-SENEC-1810' is distinguishable from *Senecio mikanioides* by the following characteristics:

1. *Senecio* 'EC-SENEC-1810' exhibits leaves having a bi-colored pattern of silver-grey and green on the upper surface. In comparison, the leaves of *Senecio mikanioides* are entirely green on the upper surface.

'EC-SENEC-1810' is distinguishable from *Senecio macroglossus* by the following characteristics:

1. *Senecio* 'EC-SENEC-1810' exhibits leaves having a bi-colored pattern of silver-grey and green on the upper surface. In comparison, the leaves of Senecio macroglossus are green with a white and green vein pattern on the upper surface.
2. The leaves of *Senecio* 'EC-SENEC-1810' are heart shaped. In comparison, the leaves of *Senecio macroglossus* are arrow shaped.

'EC-SENEC-1810' is distinguishable from the female parent plant, by the following characteristics:

1. The internodes of 'EC-SENEC-1810' are shorter than the internodes of the female parent plant.
2. 'EC-SENEC-1810' has a more compact habit than the habit of the female parent plant.

'EC-SENEC-1810' is distinguishable from the male parent plant by the following characteristics:

1. The internodes of 'EC-SENEC-1810' are shorter than the internodes of the male parent plant.
2. 'EC-SENEC-1810' has a more compact habit than the habit of the male parent plant.

BRIEF DESCRIPTION OF THE DRAWING

The accompanying photograph illustrates the distinguishing traits of *Senecio* 'EC-SENEC-1810'. The photograph shows an overall view of a 40 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new Senecio cultivar named 'EC-SENEC-1810'. Data was collected in Sappemeer, Netherlands from 40 week old plants grown in a glass greenhouse in 15.0 cm. diameter containers. The time of year was Fall and the temperature range was 18-24 degrees Centigrade during the day and 18-21 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-SENEC-1810' has not been tested under all possible conditions and phenotypic differences may be observed with variations in environmental, climatic, and cultural conditions, however, without any variance in genotype.

Botanical classification: *Senecio mikanioides* 'EC-SENEC-1810'.

Annual or perennial: Perennial.

Parentage: 'EC-SENEC-1810' is a hybrid of the female parent, an unnamed *Senecio mikanioides* cultivar and the male parent an unnamed *Senecio mikanioides* cultivar.

Plant type: Potted plant.

Growth habit: Broad spreading-creeping.

Plant shape: Spreading to creeping.

Suitable container size: 7 cm. pots or larger.

Plant height to top of foliage plane: Average 7.7 cm.

Plant width: Average 50.0 cm.

Vigor: Moderate.

Growth rate: Moderate to high.

Low Temperature Tolerance: 12° Centigrade.

High Temperature Tolerance: 30° Centigrade.

Propagation: Stem cuttings.

Time to initiate roots: Cuttings are placed directly in growing containers.

Crop time: Approximately 25 weeks in the Summer and 30 weeks in the Winter in Sappemeer, Netherlands.

Root system: Fibrous.

Plant fragrance: None.

Stem:

- *Branching habit.*—Main branches grow from base with lateral branches.
- *Basal branching.*—Yes.
- *Pinching.*—Not required.
- *Number of main branches per plant.*—Average 8.
- *Number of lateral branches per plant.*—Average 8.
- *Main branch dimensions.*—Average 43.7 cm. in length and 0.175 cm. in diameter.
- *Internode length.*—Average 2.7 cm.
- *Stem shape.*—Rounded.
- *Stem luster.*—Matte.
- *Stem pubescence.*—Moderately to densely covered with very short strigose hairs, 0.02 cm. in length.
- *Stem angle.*—Main branches average 90 degrees from vertical, secondary branches average 70 degrees from main branches.
- *Stem strength.*—Moderately strong.
- *Stem color* (*young*).—148A to 148B.
- *Stem color* (*mature*).—N186C.
- *Stem color* (*old*).—191A and 198D.
- *Internode color.*—N186C.

Foliage:

- *Leaf arrangement.*—Alternate.
- *Compound or single.*—Single.
- *Quantity of leaves per main branch.*—Average 17.
- *Leaf shape.*—Reniform to near orbicular.
- *Leaf aspect.*—Flat to very slightly concave.
- *Leaf apex.*—Abrupt acute to obtuse.
- *Leaf base.*—Truncate to reniform.
- *Leaf dimensions.*—Average 3.2 cm. in length, 3.6 cm. in width and 0.2 cm. in thickness.
- *Texture* (*both surfaces*).—Glabrous.
- *Leaf luster* (*upper surface*).—Very slightly glossy.
- *Leaf luster* (*lower surface*).—Moderately glossy.
- *Pubescence* (*both surfaces*).—Absent.
- *Leaf margin.*—Dentate.
- *Leaf lobed.*—Not lobed.
- *Leaf rugose.*—Not rugose(*both surfaces*).
- *Venation pattern.*—Laciniate.
- *Young leaf color* (*upper surface*).—191B, area surrounding veins 146A.
- *Young leaf color* (*lower surface*).—148A, strongly tinged N187A.
- *Mature leaf color* (*upper surface*).—Between N189C and 198A, area surrounding veins 147A.
- *Mature leaf color* (*lower surface*).—Between N79A and N187A.
- *Vein color* (*upper surface*).—147A.
- *Vein color* (*lower surface*).—147B.

Petiole:

- *Petiole dimensions.*—Average 1.1 cm. in length, 0.175 cm. in diameter.
- *Petiole texture.*—Glabrous.
- *Petiole luster* (*upper side*).—Very slightly glossy.
- *Petiole luster* (*lower side*).—Slightly glossy.
- *Petiole pubescence.*—Absent.
- *Petiole strength.*—Low.
- *Petiole color* (*upper side*).—N186C.
- *Petiole color* (*lower side*).—N186C.

Flower: 'EC-SENEC-1810' has not produced flowers to date.

Fruit and seed: 'EC-SENEC-1810' has not produced fruit or seed to date.

Disease and pest resistance: Disease and pest resistance has not been observed.

The invention claimed is:

1. A new and distinct variety of *Senecio* plant named 'EC-SENEC-1810' as described and illustrated.

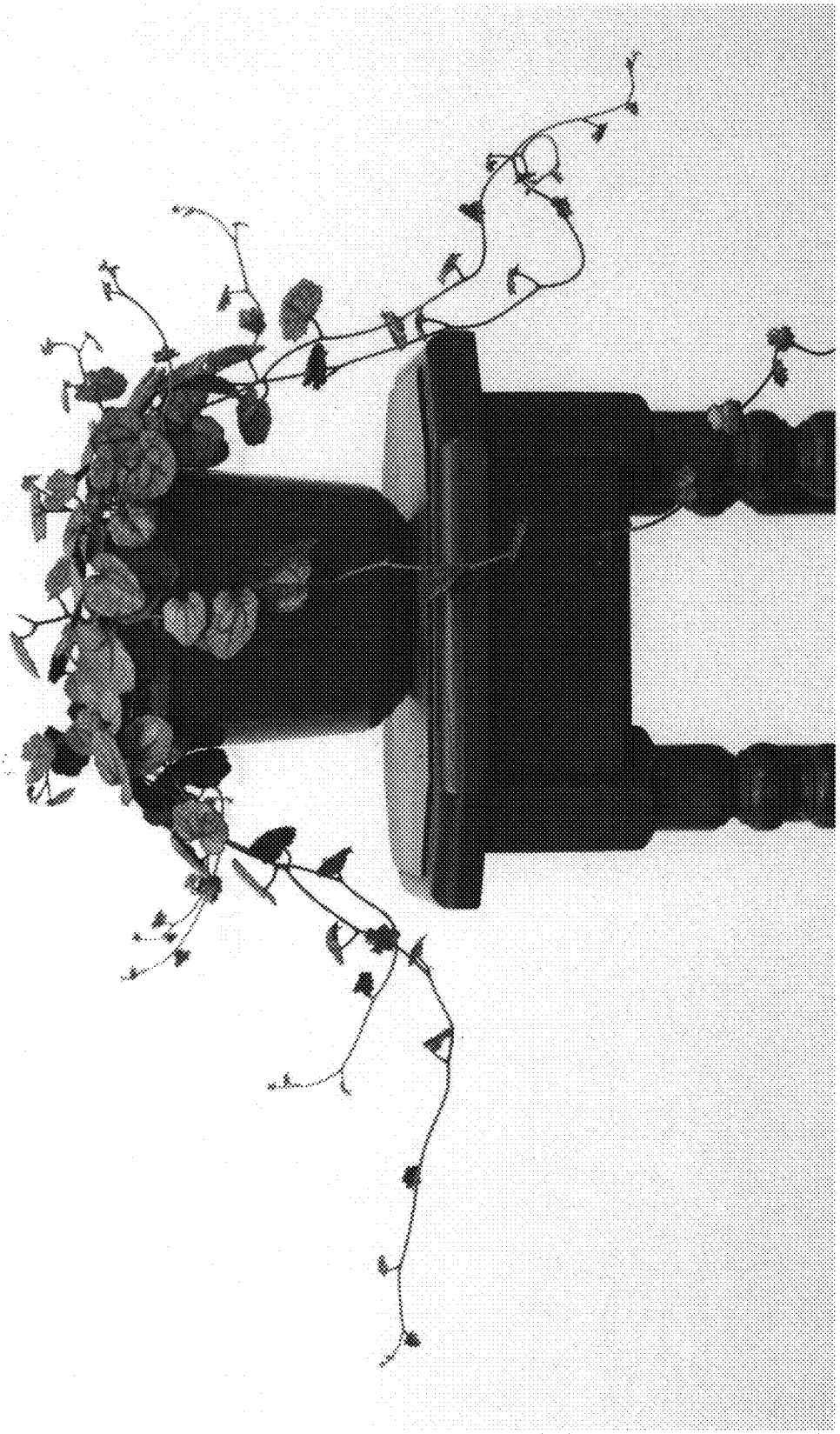

* * * * *